United States Patent [19]

Mobin-Uddin

[11] Patent Number: 5,078,735
[45] Date of Patent: Jan. 7, 1992

[54] PROSTHETIC GRAFTING METHOD FOR BYPASS SURGERY

[76] Inventor: Kazi Mobin-Uddin, 480 S. Celveland Ave., Suite 205, Westerville, Ohio 43081

[21] Appl. No.: 539,977

[22] Filed: Jun. 18, 1990

[51] Int. Cl.⁵ .............................................. A61F 2/06
[52] U.S. Cl. .................................................... 623/1
[58] Field of Search ........................................ 623/1

[56] References Cited

U.S. PATENT DOCUMENTS

| | | |
|---|---|---|
| 3,409,914 | 11/1968 | Jones . |
| 3,866,247 | 2/1975 | Sparks .................... 623/1 |
| 4,098,571 | 7/1978 | Miyata et al. . |
| 4,908,013 | 3/1990 | Muller ..................... 623/1 |
| 4,956,178 | 9/1990 | Badylak et al. ......... 623/1 |

FOREIGN PATENT DOCUMENTS 2453363  5/1976  Fed. Rep. of Germany .

OTHER PUBLICATIONS

Szilagyi et al., *Surgery* 1979, 86:836–841.
De Weese, *Surgery* 1977, 82:775–784.
Br. J. Surgery, 76:7–14, 1989.
*The Lancet*, Oct. 1, 1955, p. 711.
*Skobelkin*, Oct. 24, 1908, Derwent Abstract of Soviet Union Patent 1018–824.
*Intermedicat GMBH*, Dec. 6, 1977, Derwent Abstract of German Patent, 2852–289.
Polubudkin, *M. S. Bul.* 16, Apr. 30, 1980, Derwent Abstract of S.U. Patent 730,351.
Losev, *Bul.* 33, Sept. 5, 1977, Derwent Abstract of Soviet Union Patent 571,250.
Don Medical Inst., *Bul.* 25, Jul. 7, 1980, Derwent Abstract of Soviet Union Patent 745,508.
Don Medical Inst., *Bul.* 30, Aug. 15, 1983, Derwent Abstract of Soviet Union Patent 1034–718.
Mikhailov, *Bul.* 46, Dec. 15, 1984, Derwent Abstract of Soviet Union Patent 1128–920.
Karag Med. Inst., *Bul.* 3, Jan. 23, 1988, Derwent Abstract of Soviet Union Patent 1367–951.
Trauma Orthopaedics, *Bul.* 40, Oct. 30, 1983, Derwent Abstract of Soviet Union Patent 1050–684.

*Primary Examiner*—Randy C. Shay
*Attorney, Agent, or Firm*—Webb, Burden, Ziesenheim & Webb

[57] ABSTRACT

A prosthetic grafting method for vascular bypass surgery is disclosed wherein a section of a blood vessel which is non-functional is excised and restored for use as a blood vessel. At least one cuff is severed from the restored excised section and sutured to an end of a prosthetic graft. Alternatively, the cuff may be severed from another suitable donor vessel. The cuff and the graft are then attached to blood vessels downstream and upstream, respectively, of the now removed excised section to form a new flow passage around the formerly non-functional section.

21 Claims, 4 Drawing Sheets

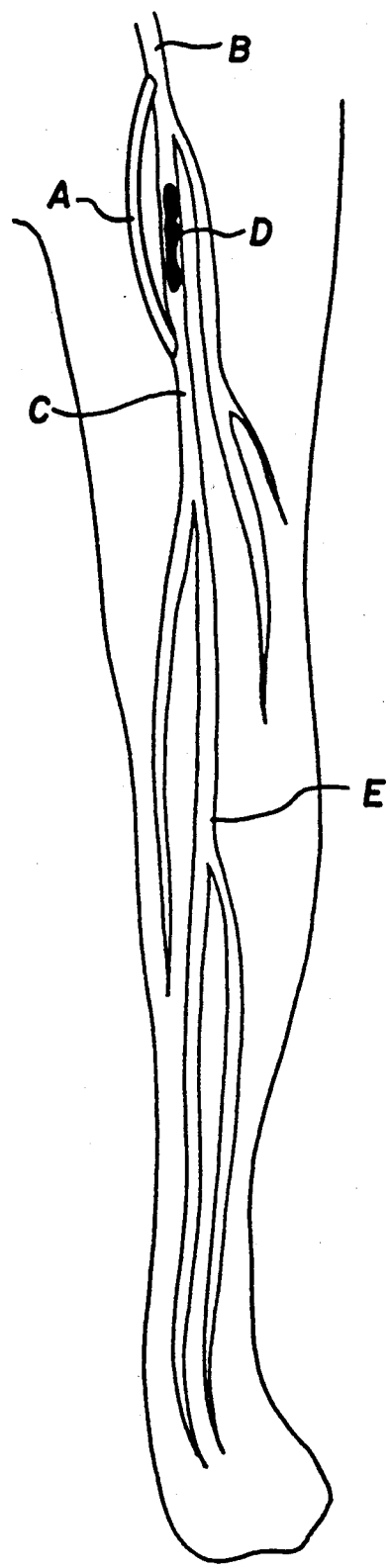
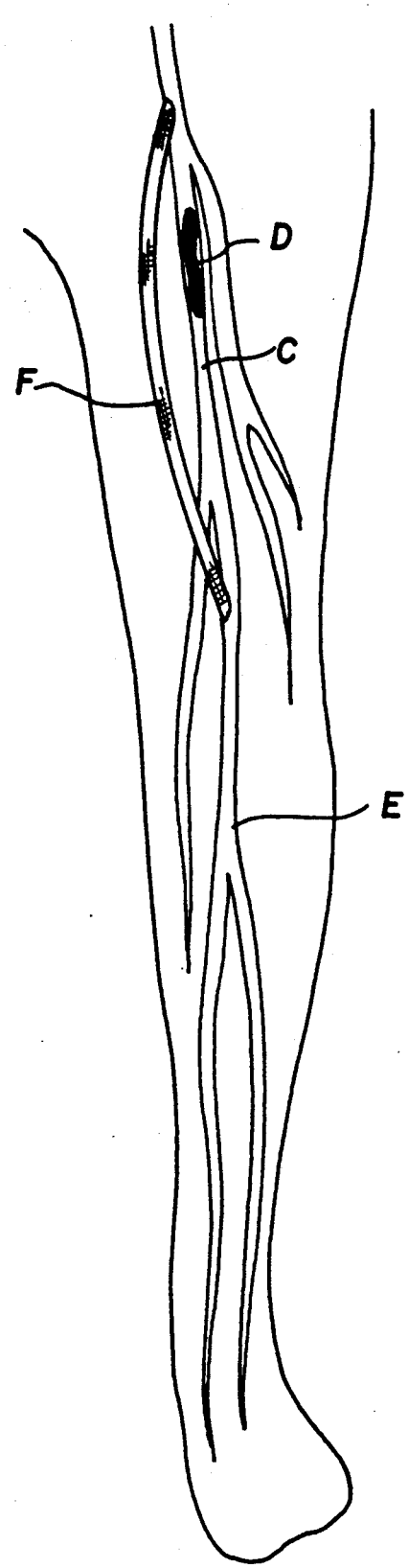
PRIOR ART
FIG. 1
PRIOR ART
FIG. 2

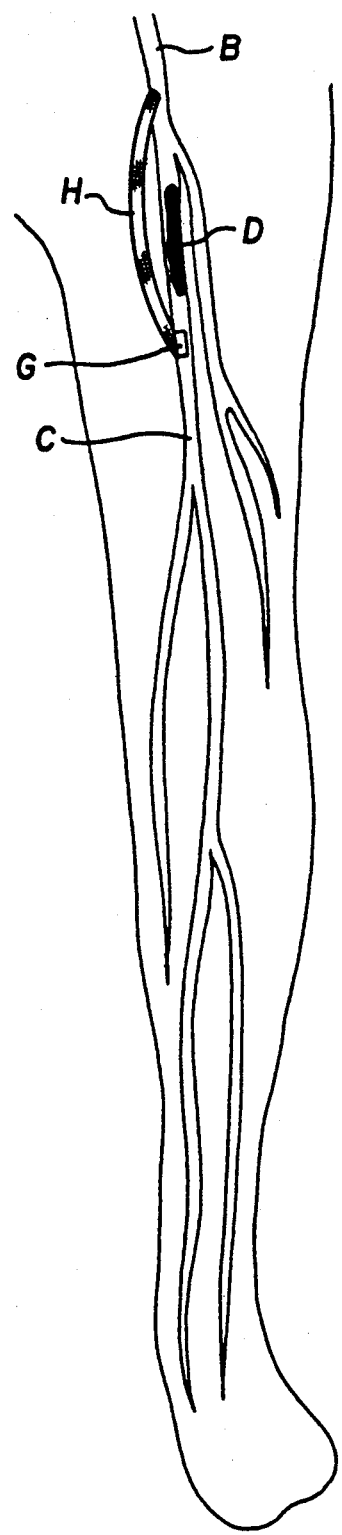
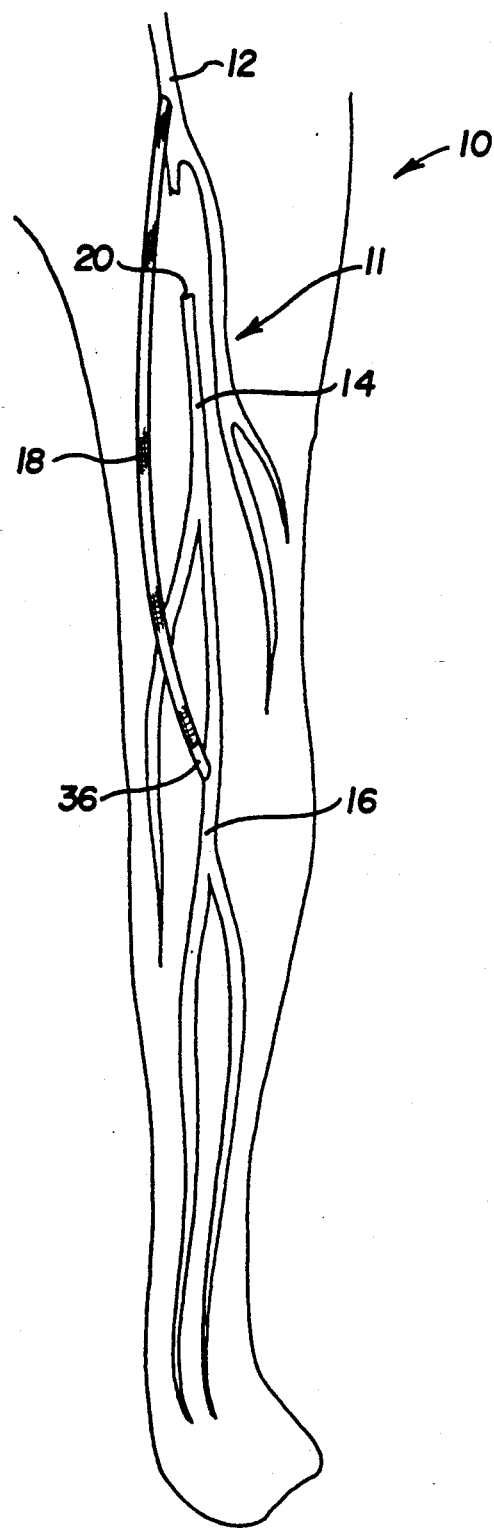
PRIOR ART
FIG. 3
FIG. 4

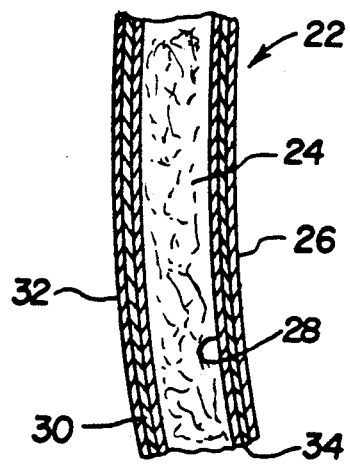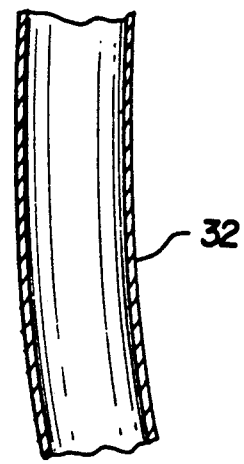
FIG. 5    FIG. 6
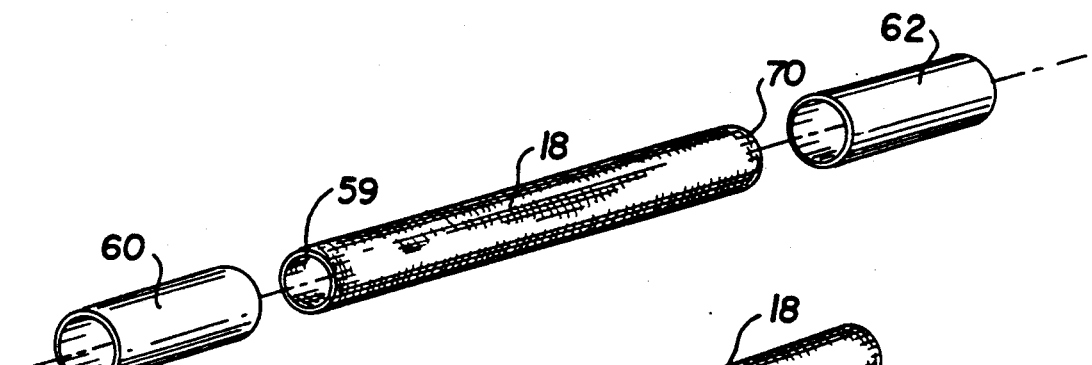
FIG. 12
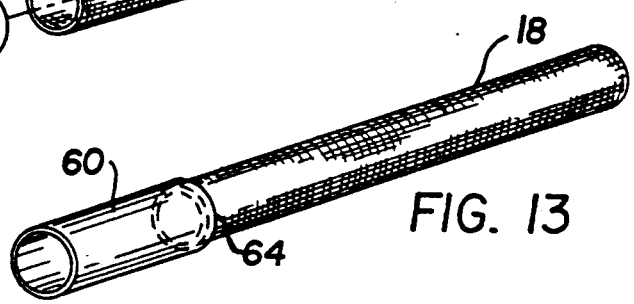
FIG. 13
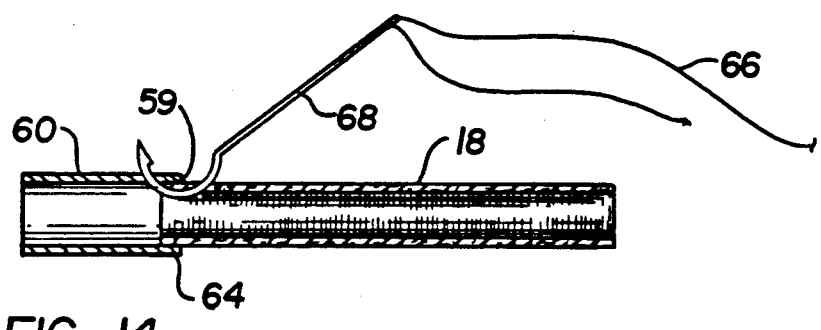
FIG. 14
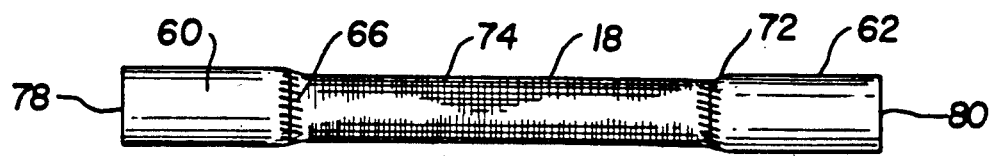
FIG. 15

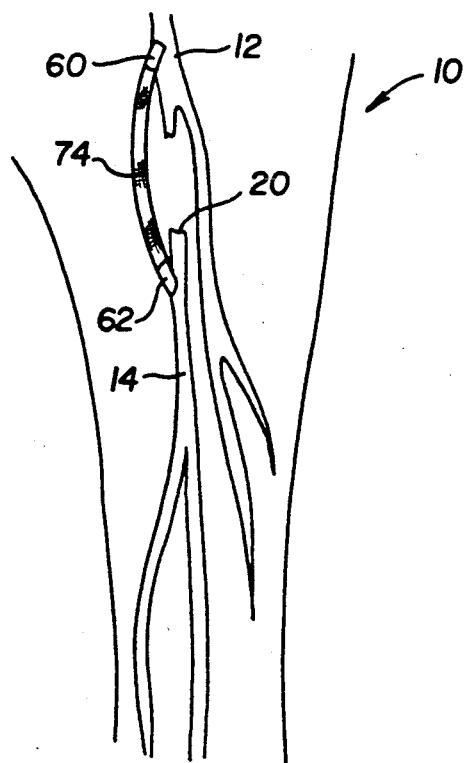
FIG. 11
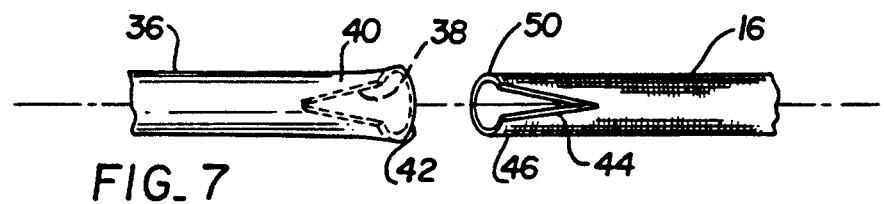
FIG. 7
FIG. 8
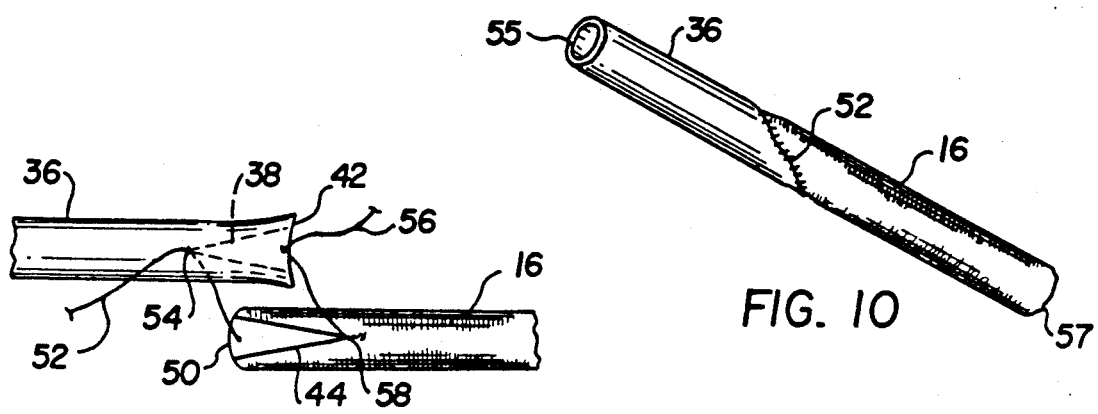
FIG. 9
FIG. 10

PROSTHETIC GRAFTING METHOD FOR BYPASS SURGERY

BACKGROUND OF THE INVENTION

1. Field of the Invention

This invention relates to grafting methods for vascular bypass surgery and, more particularly, to such methods which utilize a prosthetic graft.

2. Description of the Prior Art

A common medical problem, particularly for patients advancing in age, is atherosclerosis or hardening of the arteries. Blockage develops in the artery and restricts circulation of blood to limbs and organs. In the legs, for example, such blockage may result in gangrene and subsequent amputation of the leg. Treatment of this condition is frequently accomplished with arterial bypass surgery in which a graft is affixed to the afflicted artery to form a new flow passage around the area of blockage. In this manner, circulation to the limb or organ may be reestablished.

Initially, the practitioner must choose between using a natural blood vessel or using a prosthetic blood vessel in constructing the bypass graft. Natural blood vessel grafts, such as vein grafts, are generally preferred over prosthetic grafts because of their better long-term patency rate. Prosthetic grafts are normally used only when vein grafts are not available or not suitable. The saphenous vein, which runs under the skin from the ankle up to the groin, is often used as a natural arterial bypass graft. Referring to FIG. 1, in a common procedure known as a femoral-popliteal bypass, the saphenous vein is removed and a portion A is excised for grafting directly onto a femoral artery B and a popliteal artery C to provide for blood flow around a blockage D intermediate of the femoral and popliteal arteries.

Vein grafts, although considered the replacement of choice for reconstruction of arteries located below the groin, are known to be susceptible to structural changes after their implantation. The following structural changes have been observed in vein grafts, each possibly leading to loss of patency: (1) intimal hyperplasia-excessive thickening of the inner layer, or intima, of the blood vessel; this process may involve the anastomosis with the host artery, may be a focal lesion found anywhere along the vein graft or may be diffuse, affecting the entire graft; approximately 50% of graft failures occur due to intimal hyperplasia; (2) fibrotic thickening of the vein wall—probably due to damage to the vein during its removal, preparation and anastomosis, in combination with exposure to the high pressure arterial environment; (3) degeneration and fibrosis of the valves contained within the vein graft; (4) aneurysmal dilation of the vein graft due to intrinsic structural deficiency; and (5) Atherosclerosis. Approximately 80% of the vein grafts examined two years or more after implantation show evidence of atherosclerosis. Observation after five years has shown that 56% of femoral-popliteal bypasses appear structurally sound and functionally unimpaired. After ten years, only 44% of femoral-popliteal bypasses appear structurally sound and functionally unimpaired. Regarding femoral-tibial vein graft bypasses, it has been shown that a patency rate of 37% after five years can be expected, whereas, after eight years, this decreases to 28%. Szilagyi, et al., *Surgery* 1979, 86:836–41. DeWeese, in a similar ten year follow-up of femoral-popliteal vein grafts, reported 59% patency rate at five years and 38% at ten years. *Surgery* 1977, 82:775–84.

In patients in whom a femoral-popliteal vein bypass fails, a femoral-tibial bypass, i.e., a bypass extending further beyond the popliteal artery C to a tibial artery E, is required as is shown in FIG. 2. Since under today's common procedures, the natural vein graft had already been used for the femoral-popliteal bypass, a prosthetic graft F must be used for a femoral-tibial bypass. The results of a prosthetic femoral-tibial bypass are poor, with only 25% functional after one year.

Prosthetic grafts, when used to reconstruct arteries below the groin, have even a higher failure rate than vein grafts. The estimated five year patency rate for femoral-popliteal bypass is 61.8% using vein grafts and 43.2% using prosthetic grafts. For femoral-tibial bypass procedures, the vein graft shows a 68.4% patency rate, while the prosthetic graft shows a 26.6% patency rate. Femoral-tibial prosthetic bypass grafts generally have a less favorable prognosis as compared to femoral-tibial vein bypass grafts. *Br.J. Surgery*, 76:7–14, 1989.

Prosthetic grafts are commonly made of Polytetrafluoroethylene (PTFE) Gore-tex ® or Dacron ®. These materials are significantly stiffer or less compliant than the natural arteries to which they are affixed. A difference in mechanical properties, i.e., a compliance mismatch, thus exists at the anastomosis or connection of a prosthetic graft and an artery when the graft is constructed completely from prosthetic material. Referring again to FIG. 2, a constriction (not shown) known as anastomotic intimal hyperplasia frequently develops at the anastomosis between the prosthetic graft F and the artery, here the tibial artery E. This phenomenon is characterized by a proliferation in the production of smooth muscle cells at the anastomosis which causes a narrowing of the anastomosis, a reduction of blood flow, and a subsequent graft failure due to thrombosis. Compliance mismatch between the prosthetic material and the artery is considered to be a significant factor in the genesis of anastomotic intimal hyperplasia.

The problem of matching compliance between a graft and a host artery has long been recognized in cardiovascular surgery. For example, an article in the Oct. 1, 1955 edition of *The Lancet*, beginning at page 711, states that methods for arterial grafting involving rigid tubes may be expected to fail, particularly in areas of the body where soft tissues are mobile.

The general concept of employing a collar between the graft and the artery has been employed in anastomozing intra- and extra-peritoneal organs. One method utilizes a sealing collar made from a segment of small intestine which is free from mucous, interposing the collar between the organs and the anastomosis suture. *Skobelkin*, Oct. 24, 1980, page 31.

U.S. Pat. No. 3,409,914 to Jones discloses a connector for blood pumps and the like wherein a clothlike filler material is disposed immediately adjacent the connection between the prosthesis and the artery to permit proper in-growth of tissue. The resultant decrease in the diameter of the connection is said to increase blood flow velocity and provide a washing action at the anastomosis, which reduces the possibility of unsatisfactory clotting and/or tissue growth.

Others in the art have sought to devise a graft which itself sufficiently matches compliance with the natural artery to avoid the undesirable complications discussed above. For example, U.S. Pat. No. 4,098,571 to Miyata et al. discloses a substitute blood vessel and a process for preparing the same wherein a pig blood vessel is pretreated with a digesting solution to remove all tissue constituents except those which allow the vessel to retain collagenous and elastic fiber qualities. Similarly, the German periodical *Intermedicat GMBH* discloses in its Dec. 6, 1977 issue a process for stripping blood vessels from human umbilical cords and treating them to produce tubular prostheses.

Attempts have been made more recently to solve the problem of anastomotic intimal hyperplasia resulting from femoral-popliteal bypass surgery. As shown in FIG. 3, a vein collar G is utilized in a femoral-popliteal prosthetic bypass graft by placing the vein collar G between the prosthetic graft H and the popliteal artery C. Since the vein collar G is made from a natural blood vessel, the compliance match between the graft and the popliteal artery C is improved. Vein collar interposition decreases the rate of graft failure, but it does not eliminate the problem. Progressive intimal hyperplasia has been shown to develop in the vein collar itself.

Accordingly, it is an object of the present invention to provide a prosthetic grafting method for bypass surgery which avoids compliance mismatch and at the same time preserves potential graft blood vessels in the patient for subsequent bypass procedures.

SUMMARY OF THE INVENTION

Therefore, I have invented a method for grafting a prosthetic bypass in vascular bypass surgery which includes the steps of excising a section of a blood vessel which is non-functional, restoring the section for reuse as a blood vessel, severing at least one cuff from the excised section and securing the cuff to a first end of a prosthetic graft. The cuff is attached to and in fluid communication with a blood vessel on one side, preferably downstream, of the now removed excised section, and a second end of the prosthetic graft is attached to and in fluid communication with a blood vessel on the other side, preferably upstream, of the now removed excised section.

Alternatively, a pair of cuffs can be severed from the excised section and a cuff can be secured to each end of the prosthetic graft. The cuffs are then attached to blood vessels upstream and downstream of the now removed excised section.

The excised section is preferably restored by removing plaque and blood clot material from an interior thereof and by removing an inner layer and a middle layer from a wall thereof, leaving an outer layer intact. The cuffs are severed from the outer layer, with each cuff being substantially concentric with the outer layer. Alternatively, the cuffs may be obtained from donor blood vessels in the patient's body other than the excised section. This may be necessary in certain cases where the excised section is damaged beyond repair. These sources are well known to those skilled in the art. Donor blood vessels from others may also be used rather than blood vessels from the patient's body.

The cuffs are preferably secured to an associated end of the prosthetic graft using one of two techniques. In accordance with the first technique, each cuff is concentrically slid onto the associated end of the prosthetic graft so that a portion of the cuff overlaps the end. The cuff is then sutured to the prosthetic graft by (1) directing a needle carrying a suture first outside-in the prosthetic graft and then inside-out the cuff, (2) repeating step (1) for at least one revolution around the end of the prosthetic graft until the prosthetic graft and the cuff are fully united by the suture, and then (3) tying the suture on an exterior of the cuff to promote a smooth transition between the prosthetic graft and the cuff.

Alternatively, the cuff may be secured to the prosthetic graft by (1) making a slit in a posterior wall of one end of the cuff, (2) making a slit of similar length in an anterior wall of the first end of the prosthetic graft, (3) rounding the edges of the slit in the prosthetic graft, (4) opening the slit in the cuff, (5) positioning the slit of the cuff facing the slit of the prosthetic graft, (6) overlapping the cuff on the prosthetic graft, and (7) suturing the cuff to the prosthetic graft.

Other features and advantages of the present invention will become apparent from the following detailed description in conjunction with the accompanying drawings.

BRIEF DESCRIPTION OF THE DRAWINGS

FIG. 1 is a schematic view of the major arteries of a leg which has been provided with a femoral-popliteal bypass using a prior art grafting method;

FIG. 2 is a schematic view of a femoral-tibial bypass using a further prior art grafting method;

FIG. 3 is a schematic view of the arterial bypass of FIG. 1 using a still further prior art grafting method;

FIG. 4 is a schematic view of a femoral-tibial bypass utilizing the method of the present invention;

FIG. 5 is a cross-section of a blocked artery;

FIG. 6 is a cross-section of the artery of FIG. 5 after it has been restored for use as a blood vessel;

FIG. 7 is a perspective view of a cuff having a posterior slit and a prosthetic graft having an anterior slit;

FIG. 8 is a side view showing the cuff and the prosthetic graft of FIG. 7 after they have been opened and rounded, respectively;

FIG. 9 is a side view of the cuff of FIG. 8 being placed on top of the prosthetic graft of FIG. 8;

FIG. 10 is a perspective view of the cuff and the prosthetic graft of FIG. 8 after suturing has been completed;

FIG. 11 is a schematic view of a femoral-popliteal bypass utilizing the method of the present invention:

FIG. 12 is a perspective view of a first cuff, a prosthetic graft and a second cuff;

FIG. 13 is a perspective view of a first cuff concentrically overlapping an end of the prosthetic graft of FIG. 12;

FIG. 14 is a cross-section showing the first cuff being attached to the prosthetic graft of FIG. 13; and FIG. 15 is a side elevational view of the first cuff, second cuff and prosthetic graft shown in FIG. 12 after suturing has been completed.

DETAILED DESCRIPTION OF THE PREFERRED EMBODIMENTS

My method for grafting a prosthetic bypass in vascular bypass surgery generally comprises the steps of excising a section of a blood vessel which is nonfunctional due to plaque and blood clot material build-up, restoring that section for use as a blood vessel, and securing at least a portion of the restored excised section to a prosthetic graft. The resultant bypass structure is then attached to the nonfunctional blood vessel at positions upstream and downstream of the now removed excised section. Thus, blood flow is directed around the formerly blocked excised section to restore circulation to blood vessels which are downstream of the former location of plaque and blood clot material build-up.

The blocked portion of the blood vessel is removed by excising the vessel on either side of the blockage. After the excised section is restored, at least one cuff is severed from the excised section and secured to an associated end of the prosthetic graft. The other end of the cuff is then attached directly to the blood vessel. The use of natural blood vessel material at the point of connection of the prosthetic graft with the blood vessel reduces the occurrence of anastomotic intimal hyperplasia and subsequent failure of the graft. While the present invention will be described in connection with the femoral-tibial and femoral-popliteal bypass procedures, it will be understood that the invention is also suitable for other bypass procedures, such as aorto-femoral bypass procedures. While it is preferred to use the excised section to form the cuffs, other donor vessels could be used instead of the excised section, such as an artery from another portion of the patient's body.

Referring to FIG. 4, a human leg 10 has a vascular system 11 which includes a femoral artery 12, a popliteal artery 14, and a tibial artery 16. Utilizing my method in connection with the femoral-tibial bypass, a prosthetic blood vessel graft 18 is interposed between the femoral artery 12 and the tibial artery 16 to divert blood around an arterial section which was blocked due to plaque and blood clot material build-up. The bypassed area is shown in FIG. 4 as an open area 20, because, as discussed above, the blocked blood vessel is removed, restored and further utilized in the procedure. However, the blocked blood vessel before it is removed is shown in FIGS. 1-3.

A preferred method of restoring an excised section 22 for use as a blood vessel is shown in connection with FIGS. 5 and 6. Basically, the plaque and blood clot material 24 are first removed from the interior of the excised section 22 by known methods. The excised section 22 of the blood vessel includes a wall 26 that is composed of an intima or inner layer 28, a media or middle layer 30 and an adventitia or outer layer 32. It is the intima 28 which is afflicted with hyperplasia or smooth muscle cell proliferation when prior art prosthetic grafting methods are used. The excised section 22 is further restored for use as a blood vessel by removing the intima or inner layer 28 and media 30 from the wall 26 to limit future proliferation of smooth muscle cells. The inner layer 28 and middle layer 30 are separated from the outer layer 32 and removed by working each layer out of the interior through an end 34 of the excised section 22, leaving the outer layer 32 intact.

Referring now to FIG. 7, in the preferred variation of my method, a single cuff 36 is severed from the now restored excised section 22 using a pair of surgical scissors or the like. The shape of this cuff may differ depending upon the particularities of the procedure involved, but it is generally concentric with the outer layer 32. After the cuff 36 has been severed from the outer layer 32 of the excised section 22, it is ready for securement to the prosthetic graft 18.

Referring now to FIGS. 7-10, a slit 38 is made in a posterior wall 40 in an end 42 of the cuff 36. A slit 44 of similar length is next made in an anterior wall 46 of an end 50 of the prosthetic graft 18. Each of the slits 38, 44 will generally be about two centimeters in length. The edges created by making the slit 44 in the end 50 of the prosthetic graft 18 are next rounded by trimming with a pair of surgical scissors as shown in FIG. 8. The slit 38 in the cuff 36 is then opened, and the ends 42, 50 of the cuff 36 and the prosthetic graft 18 are positioned so that the slit 38 of the cuff 36 faces the slit 44 of the prosthetic graft 18.

A suture 52 is then directed by a needle first outside-in the end 50 of the prosthetic graft 18 and then inside-out the cuff 36 at an apex 54 of the slit 38. A second suture 56 is directed outside-in the prosthetic graft 18 at an apex 58 of the slit 44 and then inside-out the end 42 of the cuff 36. The sutures 52, 56 are then drawn to bring the end 42 of the cuff 36 in contact with the apex 58 and the prosthetic graft 18, as well as bringing the apex 54 in the cuff 36 into contact with the end 50 of the prosthetic graft 18.

The edges of the slit 38 in the cuff 36 are then overlapped on the end 50 of the prosthetic graft 18. The sutures 52, 56 are then directed first outside-in the prosthetic graft 18 and then inside-out the cuff 36 along the overlapping edges of the slit 38 and the end 42 of the cuff 36. This stitch is repeated until the cuff 36 and the prosthetic graft 18 are fully united by the sutures 52, 56 as shown in FIG. 10. The pliability of the cuff 36 allows its edges to be readily fitted to the profile of the slit 44 of the prosthetic graft 18. With the edges of the slit 38 and the end 42 of the cuff 36 on the exterior of the prosthetic graft 18, there is a smooth transition between the prosthetic graft and the cuff within the interior. This preferred variation of my method for joining the cuff to the prosthetic graft is known as a side-to-side anastomosis, and it is advantageous in that any intimal hyperplasia that may develop will not be circumferential and thus will not significantly affect blood flow.

A further variation of my invention directed to preventing intimal hyperplasia between the prosthetic graft and the cuff is to use a prosthetic graft which is eight millimeters in diameter as opposed to the usual six millimeter diameter used in common procedures. This allows for an even larger opening at the anastomosis between the prosthetic graft and the cuff, and this further insures that any anastomotic intimal hyperplasia which may develop will not significantly compromise blood flow.

Referring again to FIGS. 4 and 10, after the cuff 36 and the prosthetic graft 18 are united, a free end 55 of the cuff 36 is sutured to the subject blood vessel at a position downstream of the open area 20 in an end-to-side fashion using known methods. A free end 57 of the prosthetic graft 18 is likewise sutured to the subject vessel at a position upstream of the open area 20, thereby rerouting blood flow around the now removed excised section 22 and restoring circulation to the lower leg arteries.

FIG. 11 shows a second variation of my method. Human leg 10 is again shown with the open area 20 between the femoral artery 12 and the popliteal artery 14. The excised section 22 has been removed from the open area 20 and restored in accordance with the procedures discussed above in connection with FIGS. 5 and 6. After restoration, the outer layer 32 is severed to form two arterial cuffs, referred to as first arterial cuff 60 and second arterial cuff 62. After the arterial cuffs 60, 62 have been severed from the outer layer 32 of the excised section 22, they are attached to the prosthetic graft 18 either by a side-to-side anastomosis as discussed above, or by proceeding in the following manner.

Referring to FIGS. 12 and 13, the first cuff 60 is positioned on an end 59 of the prosthetic graft 18 by concentrically sliding the cuff 60 onto the end 59 so that a portion 64 of the cuff 60 overlaps the end 59. The first cuff 60 is then secured to the prosthetic graft at the overlapping portion 64 by a suture 66. The suture 66 is applied to the first cuff 60 by a needle 68 which, while carrying the suture 66 is directed first outside-in the end 59 of the prosthetic graft 18 then inside-out the first cuff 60. This stitching procedure is then repeated at spaced locations around the circumference of the overlapping portion 64 until the first cuff 60 is fully united to the end 59 of the prosthetic graft 18. The suture 66 is then tied on the outside of the first cuff 60. This method of securing the first cuff 60 to the prosthetic graft 18 eliminates any rough surface at the suture line within the interior of the first cuff 60 resulting in a smooth transition between the prosthetic graft 18 and the first cuff 60. This is important in the healing process and prevents development of anastomotic intimal hyperplasia between the prosthetic graft 18 and the arterial cuffs 60, 62.

The second cuff is positioned on an opposite end 70 of the prosthetic graft 18 and secured by suturing in an identical manner as described in connection with the first cuff 60. An overlapping portion 72 of the second cuff 62 is concentrically slid onto the opposite end 70 of the prosthetic graft 18 and likewise sutured. Thus, a bypass 74 is formed of the first cuff 60, the second cuff 62 and the prosthetic graft 18 as shown in FIG. 15.

The bypass 74 is then anastomozed to the femoral and popliteal arteries 12, 14 to direct blood flow around the open area 20, restoring blood circulation to the lower arteries of the leg 10. Referring again to FIG. 11, the first cuff 60 is attached to and in fluid communication with the femoral artery 12 at a location upstream of the now removed excised section 22, and the second cuff 62 is attached to and in fluid communication with the popliteal artery 14 at a position downstream of this location. A free end 78 of the first cuff 60 is sutured by known methods to the femoral artery 12 in an end-to-side fashion, and a free end 80 of the second cuff 62 is then likewise sutured to the popliteal artery 14. Thus, blood is routed around the formerly blocked area to continue through the popliteal artery 14 to the lower leg arteries.

My prosthetic grafting method for bypass surgery thus preserves natural blood vessels in the patient which may be needed for subsequent emergency grafting, while at the same time providing the advantage of placing natural arteries in anastomosis with one another. A matched anastomosis between the arterial cuffs 36, 60, 62 and the arteries 12, 14, 16 eliminates the problem of anastomotic intimal hyperplasia due to compliance mismatch. The arterial cuffs 36, 60, 62 are significantly more compliant than the prosthetic graft 18, and thus the compliance mismatch and resulting complications of the prior art grafting methods are avoided.

Compared to vein graft bypasses, which require a long incision extending from the ankle to the groin to harvest the vein graft, prosthetic bypass grafts only require two small incisions upstream and downstream. The graft is tunneled from the lower incision into the upper incision. This results in reduced operative time, reduced discomfort to the patient, and reduced risk due to exposure of the patient to anesthetic. Also, there is reduced post-operative edema of the leg following prosthetic bypass graft, as compared to the vein bypass graft.

The preferred variation of my method, which includes placement of a single arterial cuff at the downstream end of the prosthetic graft via side-to-side anastomosis, addresses the problem of intimal hyperplasia at the downstream end of the prosthetic graft where smooth muscle cell proliferations are more common. As blood flows through the prosthetic graft and into the arterial cuff, the transition is smooth due to overlapping of the cuff on the prosthetic graft. Additionally, the side-to-side anastomosis creates a wide opening at the anastomosis which further reduces the consequences of any subsequent development of intimal hyperplasia.

Each variation of my method is simple to execute and inexpensive to complete in that the arterial cuffs are derived from a section of the host artery which was blocked due to plaque and blood clot build-up. The clotted portion of the artery can be removed, the cuffs secured to the prosthetic graft and the bypass anastomozed to the afflicted blood vessels all in one procedure.

Having described the presently preferred steps for utilizing my prosthetic grafting method for bypass surgery, it will be understood that this description is not intended to limit the scope of the invention except as set forth in the appended claims.

I claim:

1. A method for grafting a prosthetic bypass in vascular bypass surgery comprising the steps of:
   a) excising a section of a nonfunctional blood vessel to by bypassed;
   b) obtaining a suitable donor vessel;
   c) severing a cuff from the donor vessel;
   d) securing said cuff to a first end of a prosthetic graft;
   e) attaching said cuff to and in fluid communication with a blood vessel on one side of the now removed excised section; and
   f) attaching a second end of said prosthetic graft to and in fluid communication with a blood vessel on the other side of the now removed excised section.

2. A method for grafting a prosthetic bypass in vascular bypass surgery comprising the steps of:
   a) excising a section of a nonfunctional blood vessel to be bypassed;
   b) restoring the excised section for reuse as a blood vessel;
   c) severing a cuff from the excised section;
   d) securing said cuff to a first end of a prosthetic graft;
   e) attaching said cuff to and in fluid communication with a blood vessel on one side of the now removed excised section; and
   f) attaching a second end of said prosthetic graft to and in fluid communication with a blood vessel on the other side of the now removed excised section.

3. The method of claim 2 wherein said cuff is attached to a blood vessel downstream of the now removed excised section and wherein the second end of said prosthetic graft is attached to a blood vessel upstream of the now removed excised section.

4. The method of claim 2 wherein said excised section is restored by removing plaque and blood clot material from an interior thereof.

5. The method of claim 4 wherein said excised section is further restored by removing an inner layer and a middle layer from a wall of said excised section, leaving an outer layer intact.

6. The method of claim 5 wherein said cuff is severed from the outer layer of said excised section, with said cuff being substantially concentric with the outer layer.

7. The method of claim 2 wherein said cuff is secured to the first end of said prosthetic graft by concentrically sliding said cuff onto said first end so that a portion of said cuff overlaps the first end and suturing the overlapping portion of said cuff to said prosthetic graft.

8. The method of claim 7 wherein said cuff is sutured to said prosthetic graft by:
   (a) directing a needle carrying a suture first outside-in said prosthetic graft and then inside-out said cuff;
   (b) repeating step (1) for at least one revolution around the first end of said prosthetic graft until said prosthetic graft and said cuff are fully united by the suture; and
   (c) then tying the suture on an exterior of said cuff to promote a smooth transition between said prosthetic graft and said cuff.

9. The method of claim 2 wherein said cuff is secured to the first end of said prosthetic graft by:
   (a) making a slit in a posterior wall of one end of said cuff;
   (b) making a slit of similar length in an anterior wall of the first end of said prosthetic graft;
   (c) rounding the edges of the slit in said prosthetic graft;
   (d) opening the slit in said cuff;
   (e) positioning the slit of said cuff facing the slit of said prosthetic graft;
   (f) overlapping said cuff on said prosthetic graft; and
   (g) suturing said cuff to said prosthetic graft.

10. A method for grafting a prosthetic bypass in vascular bypass surgery comprising the steps of:
    (a) excising a section of a nonfunctional blood vessel to be bypassed;
    (b) restoring the excised section for reuse as a blood vessel;
    (c) severing a first cuff and a second cuff from the excised section;
    (d) securing said first cuff to a first end of a prosthetic graft;
    (e) securing said second cuff to a second end of said prosthetic graft;
    (f) attaching said first cuff to and in fluid communication with a blood vessel upstream of the now removed excised section; and
    (g) attaching said second cuff to and in fluid communication with a blood vessel downstream of the now removed excised section.

11. The method of claim 10 wherein said excised section is restored by removing plaque and blood clot material from an interior thereof.

12. The method of claim 11 wherein said excised section is further restored by removing an inner layer and a middle layer from a wall of said excised section, leaving an outer layer intact.

13. The method of claim 12 wherein said first cuff and second cuff are severed from the outer layer of said excised section, with said first cuff and second cuff being substantially concentric with the outer layer.

14. The method of claim 10 wherein said first cuff and second cuff are each secured to an associated end of said prosthetic graft by concentrically sliding said cuff onto the end so that a portion of said cuff overlaps the end, and suturing the overlapping portion of said cuff to said prosthetic graft.

15. The method of claim 14 wherein said first cuff and second cuff are each sutured to said prosthetic graft by:
    (a) directing a needle carrying a suture first outside-in said prosthetic graft and then inside-out said cuff;
    (b) repeating step (1) for at least one revolution around the end of said prosthetic graft until said prosthetic graft and said cuff are fully united by the suture; and
    (c) then tying the suture on an exterior of said cuff to promote a smooth transition between said prosthetic graft and said cuff.

16. The method of claim 10 wherein said first cuff and second cuff are each secured to an associated end of said prosthetic graft by:
    (a) making a slit in a posterior wall of one end of each cuff;
    (b) making a slit of similar length in an anterior wall of the associated end of said prosthetic graft;
    (c) rounding the edges of each slit in said prosthetic graft;
    (d) opening the slit in each cuff;
    (e) positioning the slit of each cuff facing the associated slit in said prosthetic graft;
    (f) overlapping each cuff on said prosthetic graft; and
    (g) suturing each cuff to said prosthetic graft.

17. A method for grafting a prosthetic bypass in vascular bypass surgery comprising the steps of:
    (a) excising a section of a nonfunctional blood vessel to be bypassed;
    (b) restoring the excised section for reuse as a blood vessel;
    (c) severing a cuff from the excised section;
    (d) securing said cuff to a first end of a prosthetic graft by:
       (1) making a slit in a posterior wall of one end of said cuff;
       (2) making a slit of similar length in an anterior wall of the first end of said prosthetic graft;
       (3) rounding the edges of the slit in said prosthetic graft;
       (4) opening the slit in said cuff;
       (5) positioning the slit of said cuff facing the slit of said prosthetic graft;
       (6) overlapping the slit of said cuff on the slit of said prosthetic graft; and
       (7) suturing said cuff to said prosthetic graft;
    (e) attaching said cuff to and in fluid communication with a blood vessel on one side of the now removed excised section; and
    (f) attaching a second end of said prosthetic graft to and in fluid communication with a blood vessel on the other side of the now removed excised section.

18. The method of claim 17 wherein said cuff is attached to a blood vessel downstream of the now removed excised section and wherein the second end of said prosthetic graft is attached to a blood vessel upstream of the now removed excised section.

19. The method of claim 17 wherein said excised section is restored by removing plaque and blood clot material from an interior thereof.

20. The method of claim 19 wherein said excised section is further restored by removing an inner layer and a middle layer from a wall of said excised section, leaving an outer layer intact.

21. The method of claim 20 wherein said cuff is severed from the outer layer of said excised section, with said cuff being substantially concentric with the outer layer.

* * * * *